(12) United States Patent
Xu et al.

(10) Patent No.: US 7,995,702 B2
(45) Date of Patent: Aug. 9, 2011

(54) SYSTEM AND METHOD OF DATA INTERPOLATION IN FAST KVP SWITCHING DUAL ENERGY CT

(75) Inventors: Dan Xu, Schenectady, NY (US); David Allen Langan, Clifton Park, NY (US); Xiaoye Wu, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/547,117

(22) Filed: Aug. 25, 2009

(65) Prior Publication Data

US 2011/0052022 A1    Mar. 3, 2011

(51) Int. Cl.
    *A61B 6/00*    (2006.01)
(52) U.S. Cl. .................................. 378/4; 378/5
(58) Field of Classification Search ............. 378/4, 5
    See application file for complete search history.

(56) References Cited

U.S. PATENT DOCUMENTS

| | | | |
|---|---|---|---|
| 5,841,833 A | 11/1998 | Mazess et al. | |
| 6,120,951 A | 9/2000 | Klein et al. | |
| 6,522,712 B1 * | 2/2003 | Yavuz et al. | 378/4 |
| 6,614,874 B2 | 9/2003 | Avinash | |
| 6,836,528 B2 | 12/2004 | Reddy et al. | |
| 6,848,827 B2 | 2/2005 | Wu et al. | |
| 6,904,118 B2 | 6/2005 | Wu et al. | |
| 6,904,120 B2 | 6/2005 | Wu et al. | |
| 7,031,426 B2 | 4/2006 | Iatrou et al. | |
| 7,086,780 B2 | 8/2006 | Wu et al. | |
| 7,260,172 B2 | 8/2007 | Arenson et al. | |
| 7,272,429 B2 | 9/2007 | Walker et al. | |
| 7,280,631 B2 | 10/2007 | De Man et al. | |
| 7,283,605 B2 | 10/2007 | Sainath et al. | |
| 7,298,812 B2 | 11/2007 | Tkaczyk et al. | |
| 7,308,073 B2 | 12/2007 | Tkaczyk et al. | |
| 7,346,203 B2 | 3/2008 | Turek et al. | |
| 7,379,527 B2 | 5/2008 | Wu et al. | |
| 7,391,844 B2 | 6/2008 | Wu et al. | |
| 7,433,443 B1 | 10/2008 | Tkaczyk et al. | |
| 7,466,793 B2 | 12/2008 | Wu et al. | |
| 7,492,855 B2 | 2/2009 | Hopkins et al. | |

(Continued)

OTHER PUBLICATIONS

Bertram et al., Directional Interpolation of Sparsely Sampled Cone-beam CT Sinogram Data, IEEE, 2004, pp. 928-931.*

*Primary Examiner* — Edward J Glick
*Assistant Examiner* — Alexander H Taningco
(74) *Attorney, Agent, or Firm* — Scott J. Asmus (57) ABSTRACT

A CT system includes a rotatable gantry having an opening for receiving an object to be scanned, an x-ray source coupled to the gantry and configured to project x-rays through the opening, a generator configured to energize the x-ray source to a first kVp and to a second kVp to generate the x-rays, and a detector having pixels therein, the detector attached to the gantry and positioned to receive the x-rays. The system includes a computer programmed to acquire a first view dataset and a second view dataset with the x-ray source energized to the first kVp, interpolate the first and second view datasets to generate interpolated pixels in an interpolated view dataset at the first kVp, using at least two pixels from each of the first and second view datasets to generate each interpolated pixel in the interpolated view dataset, and generate an image of the object using the interpolated view dataset.

21 Claims, 9 Drawing Sheets

U.S. PATENT DOCUMENTS

| | | |
|---|---|---|
| 2003/0081821 A1* | 5/2003 | Mertelmeier et al. ........ 382/131 |
| 2003/0147497 A1* | 8/2003 | Avinash ....................... 378/98.9 |
| 2004/0081280 A1* | 4/2004 | Avinash ....................... 378/98.9 |
| 2006/0109950 A1* | 5/2006 | Arenson et al. ................... 378/4 |
| 2006/0109951 A1* | 5/2006 | Popescu ............................ 378/4 |
| 2007/0237288 A1* | 10/2007 | Tkaczyk et al. ................... 378/5 |
| 2009/0092219 A1* | 4/2009 | Wu et al. ........................... 378/5 |
| 2009/0097611 A1* | 4/2009 | Nishide et al. .................... 378/5 |
| 2009/0154787 A1* | 6/2009 | Bertram et al. ............... 382/132 |

* cited by examiner

SYSTEM AND METHOD OF DATA INTERPOLATION IN FAST KVP SWITCHING DUAL ENERGY CT

BACKGROUND OF THE INVENTION

Embodiments of the present invention relate generally to diagnostic imaging and, more particularly, to an apparatus and method of interpolating scan data from dual energy scans.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces an electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy and discharges the light energy to a photodiode adjacent thereto. Each photodiode detects the light energy and generates a corresponding electrical signal. The outputs of the photodiodes are then transmitted to the data processing system for image reconstruction.

Generally, in the absence of object scatter, a system derives behavior at a different energy based on a signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials, or the effective atomic number distribution with the scanned object.

Techniques to obtain energy sensitive measurements comprise: (1) scan with two distinctive energy spectra, and (2) detect photon energy according to energy deposition in the detector. Such measurements provide energy discrimination and material characterization, and may be used to generate reconstructed images using a basis material decomposition (BMD) algorithm. A conventional BMD algorithm is based on the concept that, in an energy region for medical CT, the x-ray attenuation of any given material can be represented by a proper density mix of two materials with distinct x-ray attenuation properties, referred to as the basis materials. The BMD algorithm computes two CT images that represent the equivalent density of one of the basis materials based on the measured projections at high and low x-ray photon energy spectra, respectively.

A principle objective of energy sensitive scanning is to obtain diagnostic CT images that enhance information (contrast separation, material specificity, etc.) within the image by utilizing two scans at different chromatic energy states. A number of techniques have been proposed to achieve energy sensitive scanning including acquiring two scans either (1) back-to-back sequentially in time where the scans require two rotations of the gantry around the subject, or (2) interleaved as a function of the rotation angle requiring one rotation around the subject, in which the tube operates at, for instance, 80 kVp and 140 kVp potentials.

High frequency generators have made it possible to switch the kVp potential of the high frequency electromagnetic energy projection source on alternating views. As a result, data for two energy sensitive scans may be obtained in a temporally interleaved fashion rather than two separate scans made several seconds apart as required with previous CT technology. However, because the low and the high energy scans are not measured simultaneously the views are misaligned from each other. In order to reconstruct images therefrom, it is desirable to have data at a given view location at both the low and high kVps. But, because of the switching operation, when for instance a view dataset at one kVp is obtained, that view location does not include data at the other kVp, and vice versa. Simple interpolations such as linear interpolation, polynomial interpolation, nearest neighbor interpolation, and the like may be employed to generate the missing data. However, such interpolation schemes may cause aliasing and other image artifacts. Further, because these interpolation schemes are essentially low pass filters, image resolution may be compromised as well.

The effect may be mitigated to an extent by increasing the number of views per rotation, the scan time, and/or the sampling frequency, as examples. However, certain applications such as cardiac do not allow longer scan time, and increasing sampling frequency in a fast kVp switching scan may result in decreased energy separation due to limited generator kVp rise and falltimes.

Therefore, it would be desirable to design an apparatus and method of data interpolation in a dual energy CT application having improved image resolution.

BRIEF DESCRIPTION OF THE INVENTION

Embodiments of the invention are directed to a method and apparatus for acquiring imaging data at more than one energy range that overcome the aforementioned drawbacks.

According to an aspect of the invention, a CT system includes a rotatable gantry having an opening for receiving an object to be scanned, an x-ray source coupled to the gantry and configured to project x-rays through the opening, a generator configured to energize the x-ray source to a first kVp and to a second kVp to generate the x-rays, and a detector having pixels therein, the detector attached to the gantry and positioned to receive the x-rays. The system includes a computer programmed to acquire a first view dataset and a second view dataset with the x-ray source energized to the first kVp, interpolate the first and second view datasets to generate interpolated pixels in an interpolated view dataset at the first kVp, using at least two pixels from each of the first and second view datasets to generate each interpolated pixel in the interpolated view dataset, and generate an image of the object using the interpolated view dataset.

According to another aspect of the invention, a method of acquiring CT imaging data includes applying a first voltage potential between a cathode and an x-ray target to generate x-rays at the first potential, applying a second voltage potential between the cathode and the x-ray target to generate x-rays at the second potential, wherein the second voltage potential is different from the first voltage potential, and obtaining a first view dataset and a second view dataset of imaging data from the x-rays generated at the first voltage potential, wherein the first view dataset and the second view dataset are obtained at respective first and second view locations that are separated by at least a third view location. The method further includes deriving a reference sinogram based on the first and second view datasets, estimating values of a third view dataset at the third view location and at the first voltage potential using pixel data from pixel locations of each of the first and second view datasets and using the reference sinogram, and reconstructing an image based on the third view dataset.

According to yet another aspect of the invention, a computer readable storage medium having stored thereon a computer program comprising instructions which when executed by a computer cause the computer to apply a first kVp potential between a cathode and a target, apply a second kVp potential, different from the first kVp potential, between the cathode and the target, and acquire a first view dataset at a first circumferential location on a CT gantry and at the first kVp potential. The computer is further caused to acquire a second view dataset at a second circumferential location on the CT gantry and at the first kVp potential, acquire a third view dataset at the second kVp potential and at a third circumferential and location on the CT gantry, wherein the third circumferential location is circumferentially located between the first circumferential location and the second circumferential location, interpolate a fourth view dataset at the third circumferential location and at the first kVp potential, wherein the interpolation includes pixels that are each interpolated with at least two pixels of data from each of the first view dataset and the second view dataset, and reconstruct an image using at least the third view dataset.

These and other advantages and features will be more readily understood from the following detailed description of preferred embodiments of the invention that is provided in connection with the accompanying drawings.

DETAILED DESCRIPTION OF THE PREFERRED EMBODIMENT

A dual energy CT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise medical imaging, security, and industrial inspection applications. In a CT application, scanning may be axial or helical. It will be appreciated by those skilled in the art that a CT implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems. The operating environment of the present invention is described with respect to a sixty-four-slice computed tomography (CT) system. However, it will be appreciated by those skilled in the art that the present invention is equally applicable for use with other multi-slice configurations.

Figure 1:
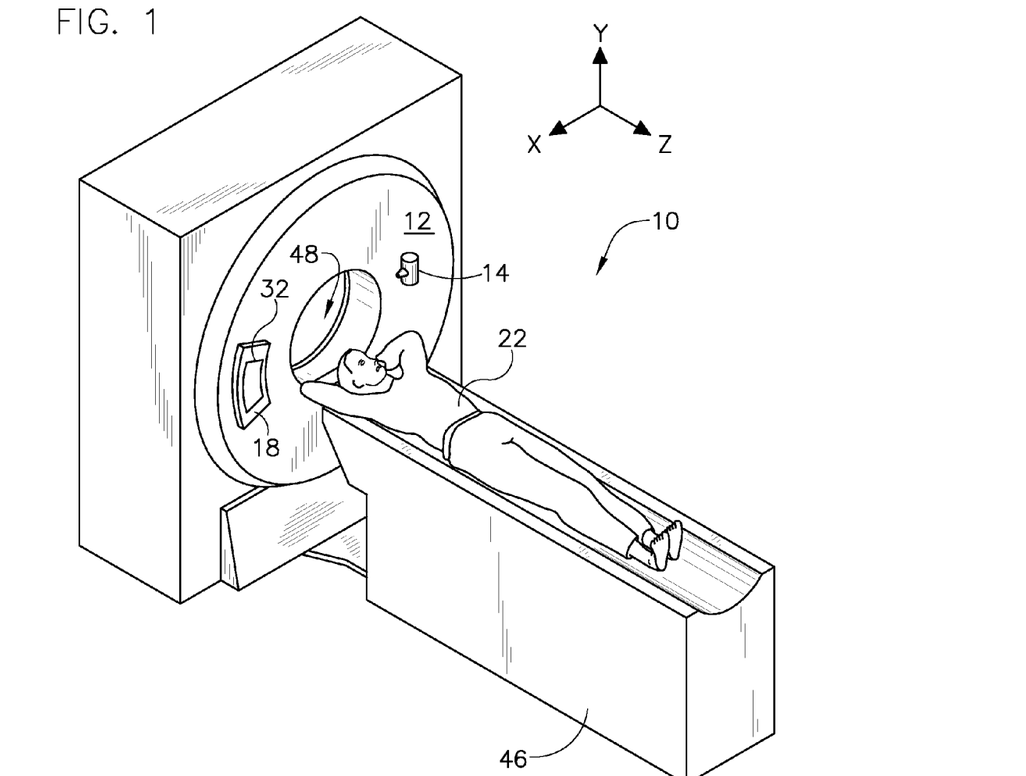
FIG. 1 is a pictorial view of a CT imaging system.
Figure 2:
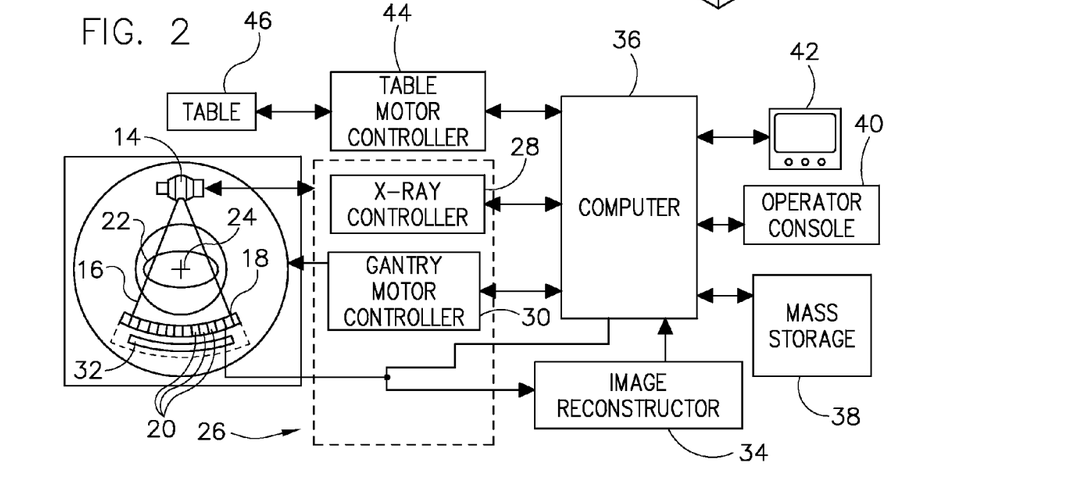
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. In embodiments of the invention, x-ray source 14 includes either a stationary target or a rotating target. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
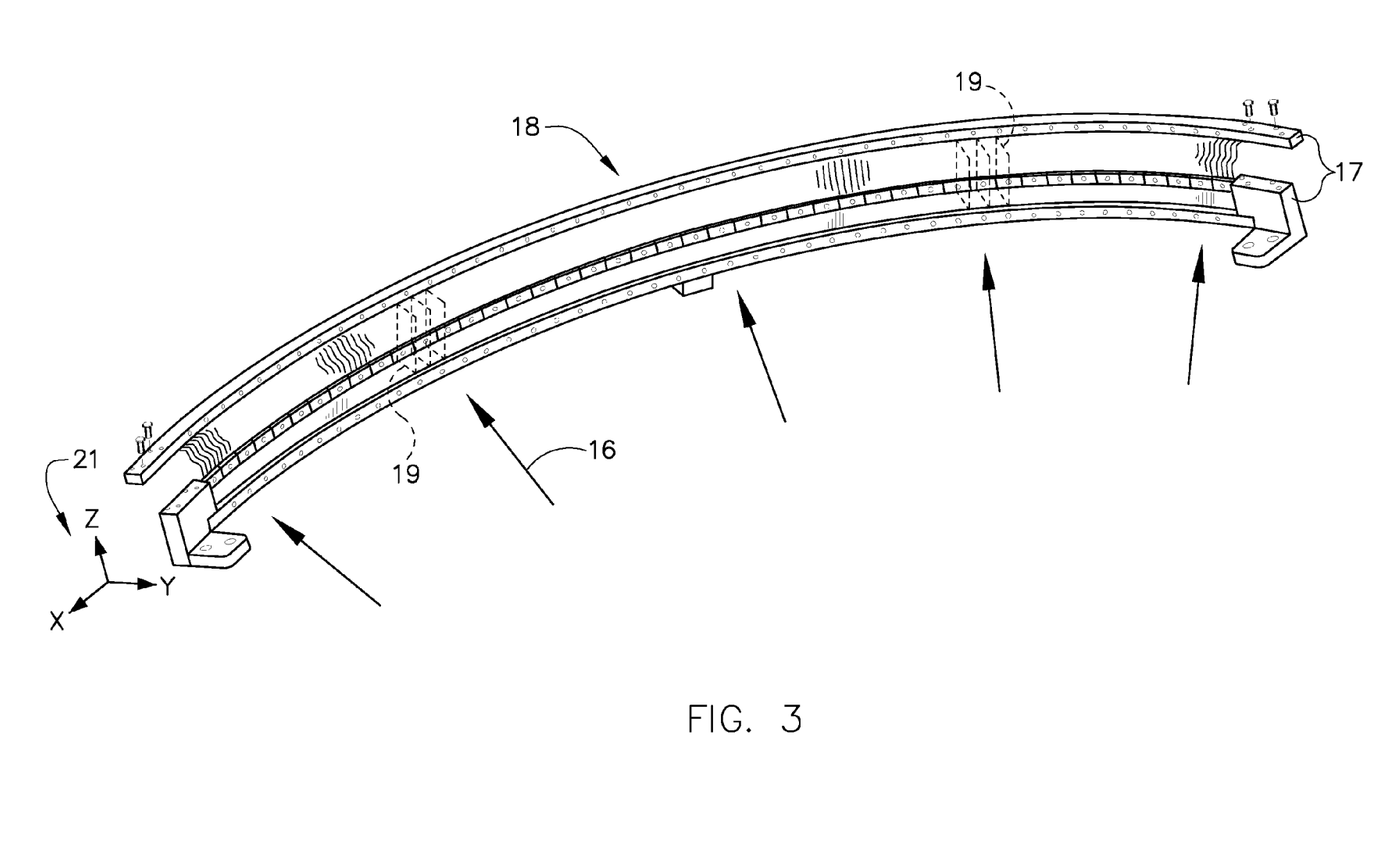
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
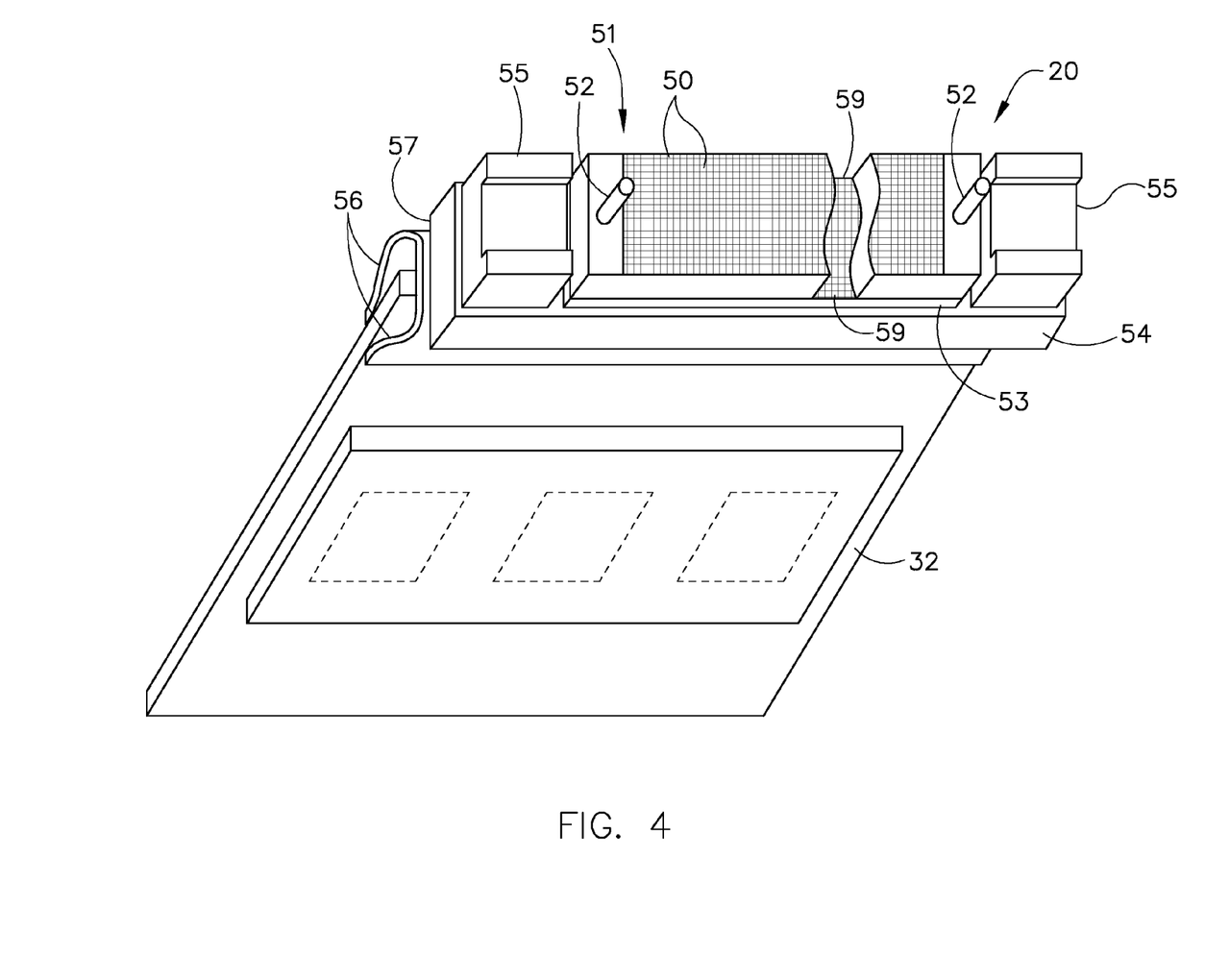
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52. In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Referring back to FIGS. 1 and 2, an illustrative discussion is now presented in connection with an exemplary implementation of a decomposition algorithm. An image or slice is computed which may incorporate, in certain modes, less or more than 360 degrees of projection data to formulate an image. The image may be collimated to desired dimensions using tungsten blades in front of x-ray source. A collimator typically defines a size and shape of beam of x-rays 16 that emerges from x-ray source 14, and a bowtie filter (not shown) may be included in system 10 to further control dose to patient 22. A typical bowtie filter attenuates beam of x-rays 16 to accommodate a body part being imaged, such as head or torso, such that, in general, less attenuation is provided for x-rays passing through or near an isocenter of patient 22. The bowtie filter shapes x-ray intensity during imaging in accordance with a region-of-interest (ROI), field of view (FOV), and/or target region of patient 22 being imaged.

As x-ray source 14 and detector array 18 rotate, detector array 18 collects data of attenuated x-ray beams. Data collected by detector array 18 undergoes pre-processing and calibration to condition the data to represent line integrals of attenuation coefficients of scanned object or patient 22. The processed data are commonly called projections. Two or more sets of projection data are typically obtained for an imaged object at different tube peak kilovoltage (kVp) levels, which change a peak and spectrum of energy of incident photons comprising emitted x-ray beams or, alternatively, at a single tube peak kVp level or spectrum with an energy resolving detector of detector array 18. The acquired sets of projection data may be used for BMD. During BMD, measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of a basis material, for example, bone, soft tissue, and/or contrast agent, in an imaged volume.

Once reconstructed, the basis material image produced by CT system 10 reveals internal features of patient 22, expressed in densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon skill and knowledge of an individual practitioner.

In addition to a CT number or Hounsfield value, an energy selective CT system can provide additional information related to a material's atomic number and density. This information may be particularly useful for a number of medical clinical applications, where a CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, any compound or mixture of materials measured with a multiple energy technique may be represented as a hypothetical material having similar x-ray energy attenuation characteristics. This hypothetical material can be assigned an effective atomic number Z. Unlike the atomic number of an element, effective atomic number of a compound is defined by its x-ray attenuation characteristics, and it need not be an integer. This effective Z representation property stems from a well-known fact that x-ray attenuation in an energy range useful for diagnostic x-ray imaging is strongly related to an electron density of compounds, which is also related to the atomic number of materials.

As stated, two or more sets of projection data are typically obtained for an imaged object at different tube peak kVp levels or potentials, and sets of projection data are typically misaligned because low and high energy scans are not measured simultaneously. Thus, high and low kVp imaging data may be acquired and interpolated to fill in missing data that occurs between switching operations, as described above.

Figure 5:
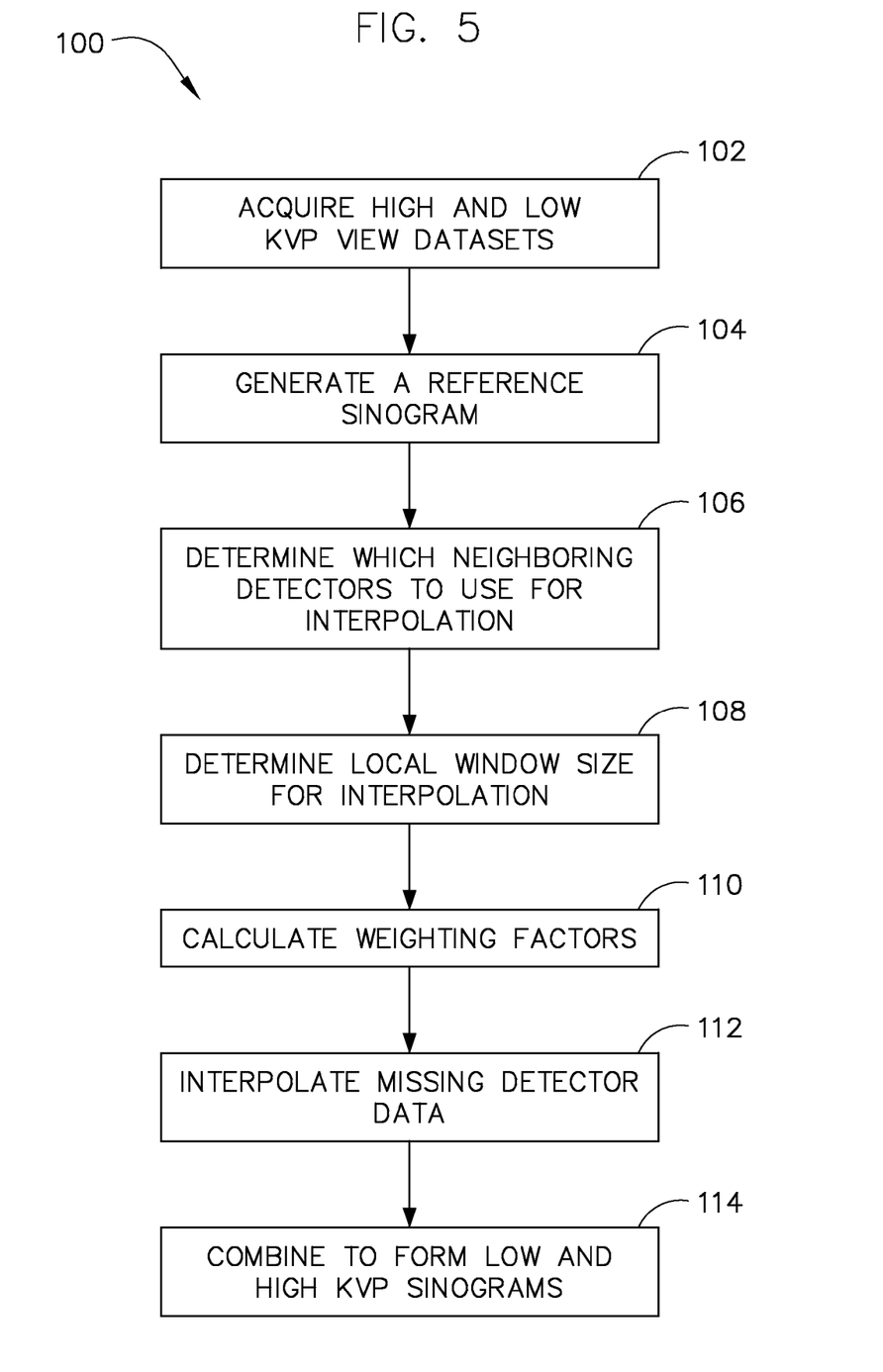
FIG. 5 is an illustration of an interpolation algorithm according to embodiments of the invention.

FIG. 5 illustrates an interpolation algorithm 100 according to embodiments of the invention. Interpolation algorithm 100 is an illustration for obtaining an interpolated dataset for each detector within a view. As will be illustrated, this interpolation algorithm 100 may be applicable to kVp switching in every other view, or may be applicable to other patterns, such as three high kVp and two low kVp view acquisitions, as an example. Regardless of the acquisition scheme chosen, such patterns result in at least one missing view dataset that may be interpolated and then combined to form high and low kVp sinograms for generating an image therefrom.

Interpolation algorithm 100 begins with acquisition of high and low kVp view datasets at step 102. From the high and low kVp view datasets acquired at step 102, a reference sinogram is generated at step 104. As will be discussed, the reference sinogram may be obtained via one of a back-projection/projection method, a combination of linearly interpolated sinograms, a local window filtering method, and a linear interpolation with Wiener filtering. Referring still to FIG. 5, depending on which acquisition scheme is being employed (one high kVp and one low kVp, three high kVp and two low kVp, etc.) and based on availability of computational resources, as examples, interpolation algorithm 100 determines which neighboring pixels to use for interpolation at step 106. At step 108 the interpolation algorithm 100 determines a local window size for performing the interpolation. The weighting factors are calculated at step 110, and the detector pixel values for missing low and high kVp view datasets are interpolated at step 112. Interpolated low kVp view datasets from step 102 are combined with interpolated high kVp datasets obtained at step 112 to form respective low and high kVp sinograms at step 114, which may be used for image reconstruction as understood within the art.

Figure 6:
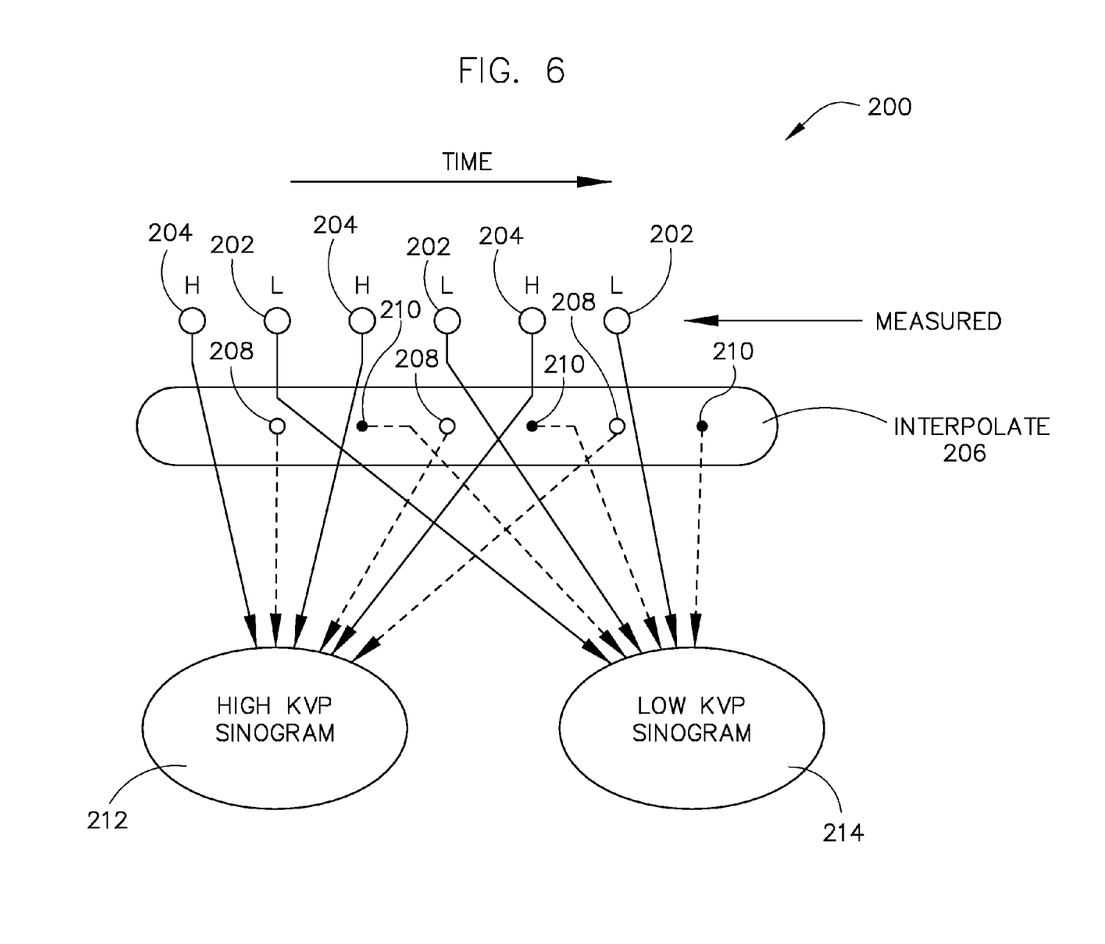
FIG. 6 illustrates a "one high and one low" scenario for data acquisition according to an embodiment of the invention.
Figure 7:
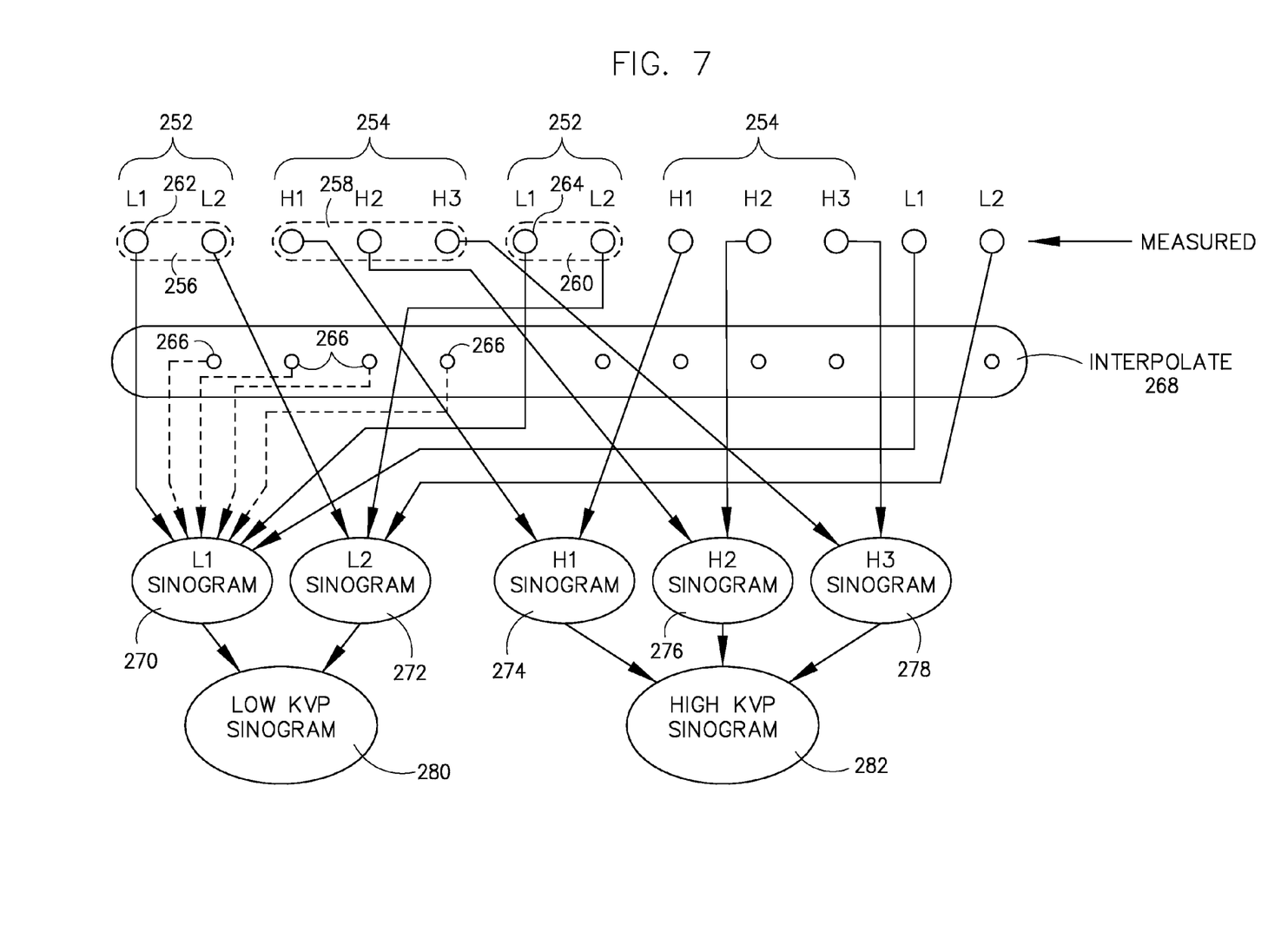
FIG. 7 illustrates a "three high and two low" scenario for data acquisition according to an embodiment of the invention.

As stated, high and low kVp data may be acquired according to different embodiments of the invention, and FIGS. 6 and 7 illustrate two scenarios of data acquisition, as examples, that may be interpolated and have an image generated therefrom, according to embodiments of the invention. In FIG. 6, data is acquired in a fast switching mode of one high kVp and one low kVp. This scenario may be for a system in which, for example, generator and overall system risetime and falltime are adequately short so as to enable switching between high and low kVp in successive views while maintaining an adequate energy separation therebetween. In FIG. 7, data is acquired in three high kVp segments and two low kVp segments. This scenario may be for a system in which, for example, generator switching and overall system risetime and falltime are not adequate to meet the imaging needs of a fast switching acquisition in successive views. Thus, the system maintains a low kVp, in the illustrated embodiment, for two views, then switches to a high kVp for three views, and the pattern repeats during data acquisition.

FIG. 6 illustrates a "one high and one low" scenario 200 that includes measurement and interpolation of low and high kVp view datasets according to an embodiment of the invention, and according to interpolation algorithm 100 described with respect to FIG. 5. In this scenario, the generator is switched between low and high kVp at each view location. Thus, acquisition of high and low kVp view datasets are interleaved, and measured low kVp datasets 202 (designated as "L") and measured high kVp datasets 204 (designated as "H") are obtained. At interpolation step 206, missing high kVp datasets 208 and missing low kVp datasets 210 are interpolated, as will be described below. After interpolation step 206, interpolated high kVp datasets 208 are merged with measured high kVp datasets 204 to form a high kVp sinogram 212 according to embodiments of the invention. Likewise, after interpolation step 206, interpolated low kVp datasets 210 are merged with measured low kVp datasets 202 to form a low kVp sinogram 214. The high and low kVp datasets 204, 202 obtained correspond to step 102 of FIG. 5, and interpolation step 206 corresponds to data interpolation at step 112 of FIG. 5.

FIG. 7 illustrates a "three high and two low" scenario 250 that includes measurement and interpolation of low and high kVp view datasets according to another embodiment of the invention. In this scenario, the generator is switched to high kVp for three sequential view locations and then switched to low kVp for two sequential view locations, and the pattern is repeated. However, because switching speeds are not instantaneous, and because some systems include a scintillator that has a response time that is in excess of the time between acquired views, each view within a sequence of views may have a different effective energy despite the generator being set to the same energy within the sequence. Thus, according to one embodiment, a subset of two low kVp view datasets 252 and a subset of three high kVp view datasets 254 are obtained according to a repeating pattern, and each view dataset may have a respective effective energy that may be identified by its position in the repeating pattern of data acquisition.

In this embodiment, view datasets having the same effective energy will be used for interpolation to form sinograms at that effective energy before combining to form high and low kVp sinograms. As an example, a first subset of two low kVp view datasets 256 (labeled L1 and L2) is obtained, and the system is switched to high kVp, and a subset of three high kVp view datasets 258 (labeled H1, H2, and H3) is obtained. The system is switched back to low kVp where a subset of two low kVp view datasets 260 (labeled L1 and L2) is obtained, and the process continues. Within each subset, similarly labeled view datasets are at the same effective energy, and the view datasets having the same effective energy are combined for the interpolation. For instance, the subset of two low kVp view datasets 256 includes a first low dataset 262 (L1), and the subsequent subset of two low kVp view datasets 260 likewise includes another first low dataset 264 (L1). Thus, according to this embodiment, each "first low dataset" 262, 264, etc. is used to generate missing view datasets 266 that correspond to an effective energy that corresponds to the measured L1 view datasets, and data having an effective L1 energy is interpolated at the other [four] view locations that occur between each measured occurrence of L1. Similarly, the measured view datasets (L2, H1, H2, H3) may be used to generate missing view datasets at respective effective energies.

As illustrated in FIG. 7, data is interpolated at step 268, but the interpolation step 268 does not result in final low or high sinograms, according to this embodiment. Instead, respective intermediate sinograms L1 270, L2 272, H1 274, H2 276, and H3 278 are formed by interpolation as described herein and by combining with respective measured view datasets at each effective energy. After formation of the intermediate sinograms 270-278, the low kVp (L1 and L2) intermediate sinograms 270, 272 may be combined to form a low kVp sinogram 280, and the high kVp (H1, H2, and H3) intermediate sinograms 274, 276, 278 may be combined to form a high kVp sinogram 282, and the combination of sinograms may be accomplished as understood within the art.

Accordingly, high and low kVp datasets may be acquired and interpolated, and high and low kVp sinograms may be formed in multiple fashions according to embodiments of the invention. The data interpolation, likewise, may be performed in multiple fashions according to embodiments of the invention. Referring back to FIG. 5, high and low kVp view datasets are acquired at step 102, and a reference sinogram is generated therefrom at step 104. According to embodiments of the invention, there are several ways to obtain the reference sinogram, which include one of a back-projection/projection method, a combination of linearly interpolated sinograms, a local window filtering method, and a linear interpolation with Wiener filtering.

Back-Projection/Projection Method

In this embodiment, the reference sinogram is obtained via back-projection of all the view data obtained. This solution typically yields good performance for axial scans, but it tends to be computationally intensive.

Combination of Linearly Interpolated Sinograms

In this method, the sinograms of individual view groups are linearly interpolated. The interpolated sinograms then are summed together to form the reference sinogram. As a result, for each view, the projection is a combination of all kVps, and the interleaving switching pattern is greatly suppressed. However, the reference sinogram may be blurred in the view direction, and any blurring may affect the interpolation quality and may not fully remove streak artifacts created by table edges.

Local Window Filtering

This method applies a local window to filter the fast switching sinogram. For example, for 3-high-2-low switching data, a 3×5 local window is applied. Similar to the combined linear interpolation method, the filtered sinogram greatly removes the switching pattern. The filtered sinogram is then multiplied by the ratio of the fast switching sinogram and its local average:

$$p_{ref} = (p \otimes W_1) \cdot \frac{p}{p \otimes W_2};$$ (EQN. 1), in which W1 is a 3×5 window and W2 is a 5×1 window.

Linear Interpolation and Wiener Filtering

The reference sinogram obtained by the combined linear interpolation is actually a convolution between the fast switching sinogram and a kernel of h=[0.04, 0.08, 0.12, 0.16, 0.20, 0.16, 0.12, 0.08, 0.04]. By carefully choosing a deconvolution kernel, the sinogram can be de-blurred along the view direction. The switching pattern is a high frequency component that can be suppressed in the deconvolution process.

Because y=x⊗h, Y=X·H, in which Y, X and H are the Fourier transforms of the convolved sinogram, the original fast switching sinogram, and the convolution kernel, respectively. The ideal deconvolution kernel is therefore 1/H=H*/H². This deconvolution kernel has infinite length in the time domain and amplifies the high frequency noise. As a result, the deconvolution kernel is usually not applied directly. Instead, a Wiener filter is frequently applied. The Wiener filter minimizes the mean square error (MSE) while deconvolving the signal:

$$G = \frac{H^*}{H^2 + K};$$ (EQN. 2), in which K is the noise-to-signal ratio in the frequency domain.

Referring back to FIG. 5, after acquiring high and low kVp view datasets at step 102 and generating a reference sinogram at step 104 as described above, the interpolation process 100 continues by determining which detectors to use for interpolation 106, determining the local window size for interpolation 108, and calculating weighting factors 110 for conducting the interpolation at step 112.

Interpolation algorithm 100 interpolates missing low and high kVp views along object directions that are extracted from the measured data. Specifically, interpolation algorithm 100 finds the minimum square error (MSE) solution, and interpolation algorithm 100 assumes that the correlation between pixels varies in the same fashion as the correlation between pixels obtained via the reference sinogram in step 104 above.

In general, the MSE can be written as:

$$MSE = \sum_i \sum_j (F_{ij} - \hat{F}_{ij})^2;$$ (EQN. 3), where $F_{ij}$ represents a weighted function from interpolation views and detectors to a detector being interpolated. The weighted function, $F_{ij}$, may be written as:

$$F_{ij} = \Sigma wF;$$ (EQN. 4), where w represents each weighting factor and each value F represents a measured detector or pixel value. $\hat{F}_{ij}$ represents a vector from interpolation views and detectors to the detector being interpolated, and makes use of the reference sinogram to find weights w such that the MSE is minimized:

$$\vec{w} = \text{argmin} \sum_i \sum_j (F_{ij} - \hat{F}_{ij})^2;$$ (EQN. 5).

The above target function defined in EQN. 5 is quadratic. Thus, in order to minimize the MSE, a derivative with respect to each weight w may be taken and set to zero, resulting in a set of equations for each weight and an array of equations:

$$\frac{\partial MSE}{\partial w} = 0;$$ (EQN. 6).

The above equation array can be simplified as:

$$C^T C \vec{w} = C^T \vec{F};$$ (EQN. 7), in which $\vec{F}$ is a vector containing the detectors in a local window of size M×M, and C is a M²×2N matrix whose kth row is the 2N neighbors of each detector in $\vec{F}$.

EQN. 7 may be used to determine weights w to optimize the interpolation in the examples provided above. In one example, as discussed with respect to FIG. 6 above, a 2-point interpolation may be performed for every view switching of a one high-one low switching scenario.

2-Point Interpolation for Every View Switching

For every view switching, $F_{ij}$ is calculated as: $\vec{F}_{ij} = w_{1k} F_{i-1,j-k} + w_{2k} F_{i+1,j-k}$ in which k ∈ {−W,−W+1, . . . , W−1, W} and N=2W+1 is the number of point pairs to be used. The selected $w_{1k}$ and $w_{2k}$ produce the smallest error of $(\vec{F}_{ij} - F_{ij})^2$ within those 2W+1 point pairs.

For each point pair, $w_{1k}$ and $w_{2k}$ are calculated by:

$$w_{1k} \Sigma F_{i-1,j+k}^2 + w_{2k} \Sigma F_{i-1,j+k} F_{i+1,j-k} = \Sigma F_{ij} F_{i-1,j+k};$$ (EQN. 8), $$w_{1k} \Sigma F_{i-1,j+k} F_{i+1,j,k} + w_{2k} \Sigma F_{i+1,j,k}^2 = \Sigma F_{ij} F_{i+1,j,k};$$ (EQN. 9), in which the summation is over a M×M local window. M+2 views (from view i−(M−1)/2−1 to view i+(M−1)/2+1) are used to calculate the weights in the above equations.

Interpolation for View Switching After Multiple Views

Figure 8:
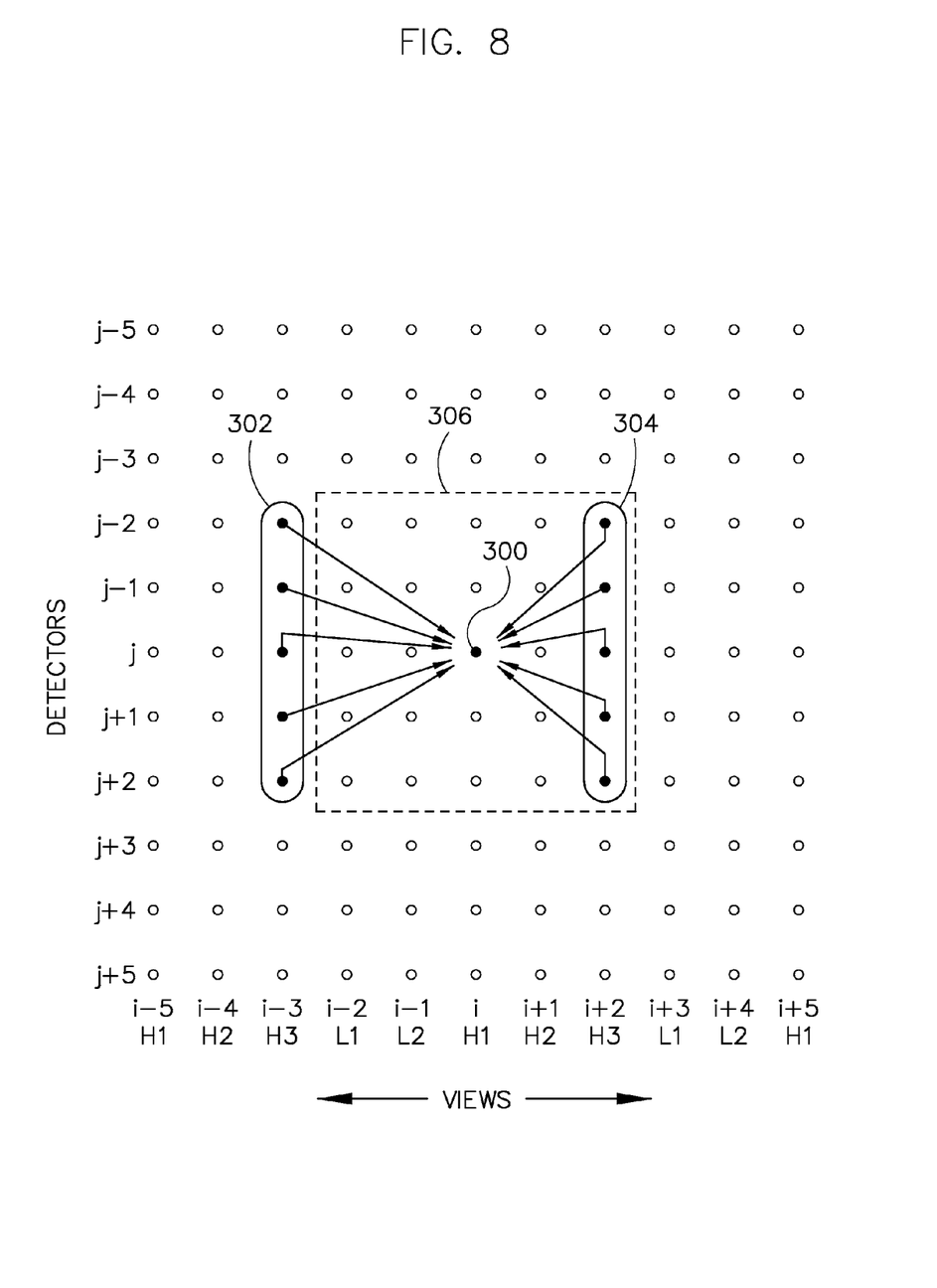
FIG. 8 illustrates data obtained in an array of detectors or pixels, according to an embodiment of the invention.

FIG. 8 represents data obtained in an array of detectors or pixels ranging from j+5 to j−5 in views i−5 to i+5 and having data acquired according to the "three high and two low" scenario discussed above with respect to FIG. 7. Referring to FIG. 8, in order to interpolate the high kVp value H3 of the $i^{th}$ view and $j^{th}$ detector 300, as an example, N×2 neighboring points from the acquired H3 data can be used. In FIG. 8, N=5, thus five sampled data points from each of the nearest H3 acquisitions is used (i.e. the five neighboring points 302 in the i−3 view, and the five neighboring points 304 in the i+2 view). Vector $F_{i,j}$ then includes a weighted function to each of the N×2 measured H2 data points, as illustrated in the following equation:

$$F_{i,j} = w_1 F_{i-3,j-2} + w_2 F_{i-3,j-1} + w_3 F_{i-3,j} + \\ w_4 F_{i-3,j+1} + w_5 F_{i-3,j+2} + w_6 F_{i+2,j-2} + \\ w_7 F_{i+2,j-1} + w_8 F_{i+2,j} + w_9 F_{i+2,j+1} + w_{10} F_{i+2,j+2};$$ (EQN. 10), and EQN. 7 ($C^T C \vec{w} = C^T \vec{F}$) is used to solve for the weighting values w. In this example, C is a $M^2 \times 10[2 \times N]$ matrix whose $k^{th}$ row is the 10 neighboring points of each pixel in a local window with size M×M, and in this example the M×M matrix is a 5×5 matrix 306, and the $\vec{F}$ vector derives from the reference sinogram, which is obtained in one of the manners described above.

Although N is illustrated as having five data points 302, 304 for performing the interpolation and the M×M matrix is illustrated as a 5×5 matrix 306, it is to be understood such are for illustrative purposes, and the interpolation and matrix sizes may vary from that illustrated. Thus, the number of points used for interpolation may be more or less than five data points, and the M×M matrix may be more or less than a 5×5 matrix according to embodiments of the invention.

2-Point Interpolation

As is evident in EQN. 7, for each point in the sinogram, a 2N×2N matrix is to be constructed and solved. For each element in the 2N×2N matrix, the sinogram is to be summed over an M×M local window, which can be computationally expensive and time-consuming. Further, the inversion of the 2N×2N matrix may also use substantial computational power.

Figure 9:
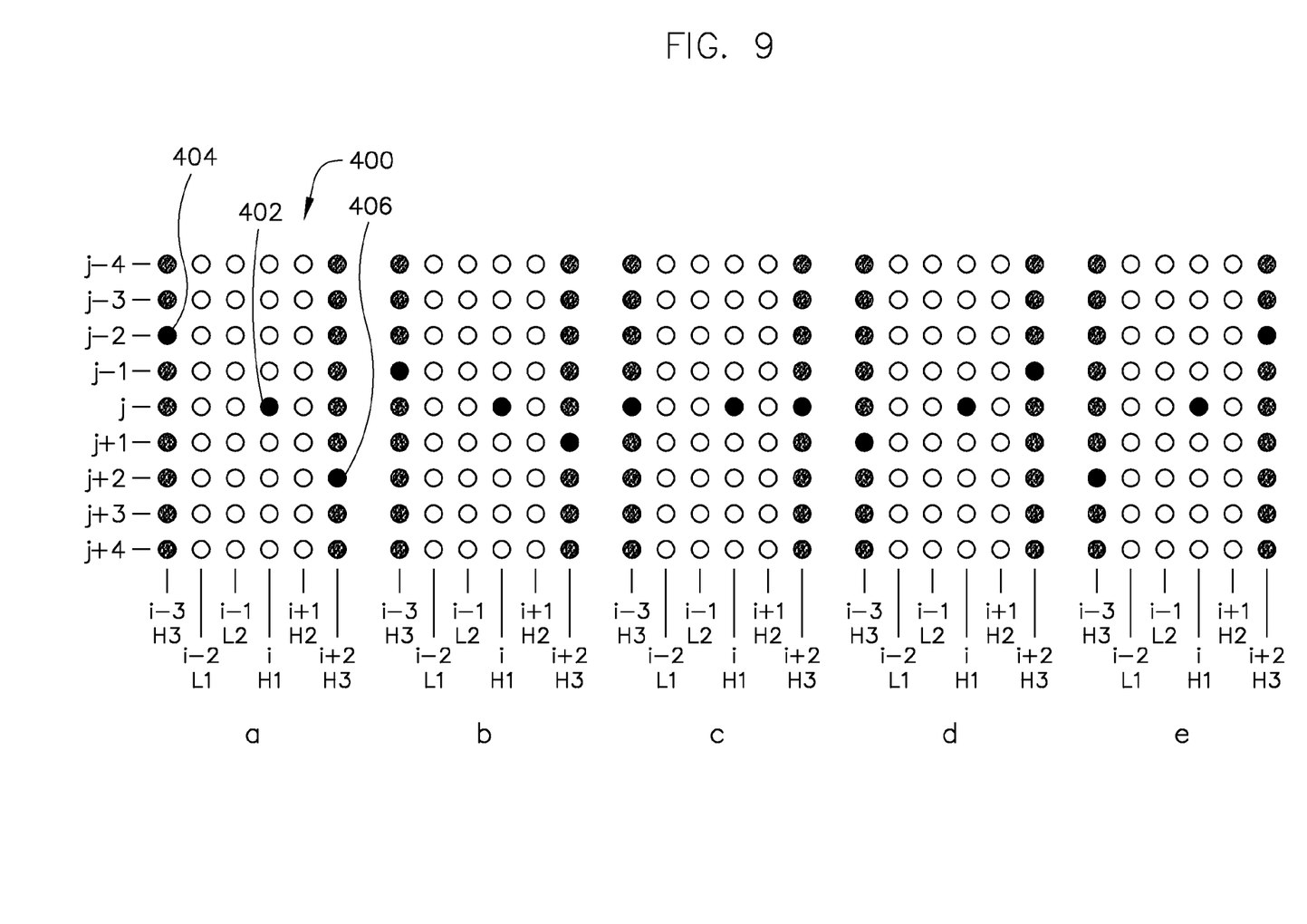
FIG. 9 illustrates 2-point interpolation according to an embodiment of the invention.

To speed up the interpolation, a 2-point interpolation is applied according to one embodiment of the invention. The total 2N neighboring pixels are grouped into N pairs, and the interpolation is individually applied to those N pairs. Within the N interpolation results, the pair with the smallest error is applied to obtain the interpolation result, and the interpolation error can be calculated from the reference sinogram. Such is illustrated in FIG. 9 (N=5, and five separate interpolations a-e are illustrated), where, within each illustration, detectors or pixels are shown from j−4 to j+4, and views i−3 to i+3 are shown, according to this embodiment.

According to this embodiment, for each pair (a-e as illustrated), only a 2×2 matrix requires to be constructed and solved. Thus, each pair illustrates a subsequent interpolation about view i and detector j that may be performed according to this embodiment. As an example and similarly to that illustrated in FIG. 8, illustrations a-e each include data acquired in a "three high and two low" scenario, and H3 data for a pixel j at view i will be interpolated, according to this embodiment, using five interpolations. Illustration "a" 400 shows a pixel or detector "j" in view "i" 402 that will be interpolated between measured H3 data at view i−3 and detector j−2 404 and measured H3 data at view i+2 and detector j+2 406. Likewise, in the additional illustrations "b" through "e," detector "j" in view "i" is interpolated other H3 data in pairs as illustrated therein.

As a result, the 2-point interpolation is at least N times faster than the above algorithm based on EQN. 7. Further, the inversion of a 2×2 matrix is a computationally simple function, thus requiring little computational power. Furthermore, the correlation between pixels can be pre-calculated from the reference sinogram to save yet more computational time.

Figure 10:
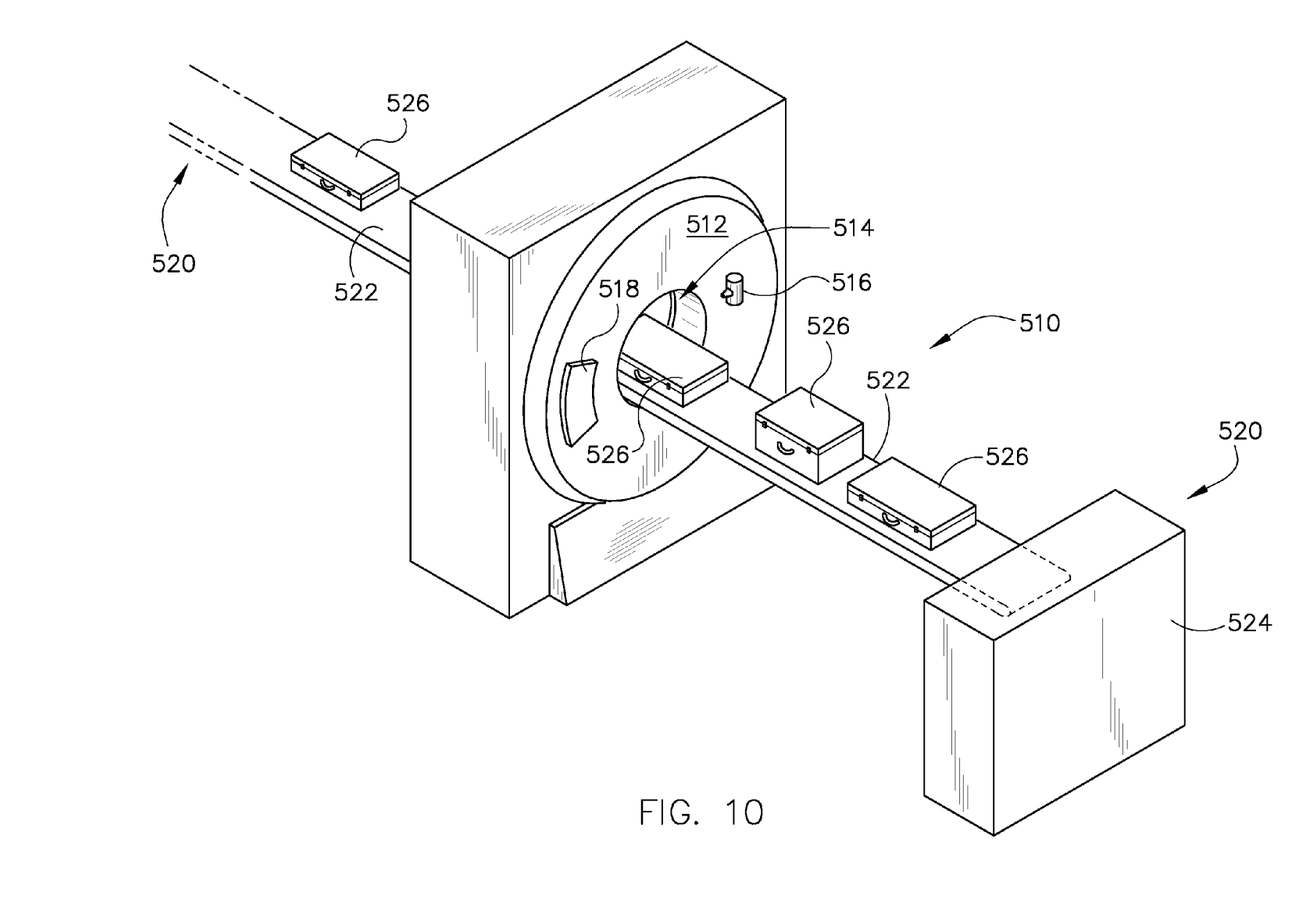
FIG. 10 is a pictorial view of a CT system for use with a non-invasive package inspection system according to an embodiment of the invention.

Referring now to FIG. 10, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network.

According to an embodiment of the invention, a CT system includes a rotatable gantry having an opening for receiving an object to be scanned, an x-ray source coupled to the gantry and configured to project x-rays through the opening, a generator configured to energize the x-ray source to a first kVp and to a second kVp to generate the x-rays, and a detector having pixels therein, the detector attached to the gantry and positioned to receive the x-rays. The system includes a computer programmed to acquire a first view dataset and a second view dataset with the x-ray source energized to the first kVp, interpolate the first and second view datasets to generate interpolated pixels in an interpolated view dataset at the first kVp, using at least two pixels from each of the first and second view datasets to generate each interpolated pixel in the interpolated view dataset, and generate an image of the object using the interpolated view dataset.

According to another embodiment of the invention, a method of acquiring CT imaging data includes applying a first voltage potential between a cathode and an x-ray target to generate x-rays at the first potential, applying a second voltage potential between the cathode and the x-ray target to generate x-rays at the second potential, wherein the second voltage potential is different from the first voltage potential, and obtaining a first view dataset and a second view dataset of imaging data from the x-rays generated at the first voltage potential, wherein the first view dataset and the second view dataset are obtained at respective first and second view locations that are separated by at least a third view location. The method further includes deriving a reference sinogram based on the first and second view datasets, estimating values of a third view dataset at the third view location and at the first voltage potential using pixel data from pixel locations of each of the first and second view datasets and using the reference sinogram, and reconstructing an image based on the third view dataset.

According to yet another embodiment of the invention, a computer readable storage medium having stored thereon a computer program comprising instructions which when executed by a computer cause the computer to apply a first kVp potential between a cathode and a target, apply a second kVp potential, different from the first kVp potential, between the cathode and the target, and acquire a first view dataset at a first circumferential location on a CT gantry and at the first kVp potential. The computer is further caused to acquire a second view dataset at a second circumferential location on the CT gantry and at the first kVp potential, acquire a third view dataset at the second kVp potential and at a third circumferential and location on the CT gantry, wherein the third circumferential location is circumferentially located between the first circumferential location and the second circumferential location, interpolate a fourth view dataset at the third circumferential location and at the first kVp potential, wherein the interpolation includes pixels that are each interpolated with at least two pixels of data from each of the first view dataset and the second view dataset, and reconstruct an image using at least the third view dataset.

A technical contribution for the disclosed method and apparatus is that it provides for a computer-implemented apparatus and method of diagnostic imaging and of interpolating scan data from dual energy scans.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A CT system comprising:
   a rotatable gantry having an opening for receiving an object to be scanned;
   an x-ray source coupled to the gantry and configured to project x-rays through the opening;
   a generator configured to energize the x-ray source to a first kVp and to a second kVp to generate the x-rays, wherein said first kVp is different than said second kVp;
   a detector having pixels therein, the detector attached to the gantry and positioned to receive the x-rays; and
   a computer programmed to:
      acquire a first view dataset and a second view dataset with the x-ray source energized to the first kVp and second kVp respectively;
      generate a reference sinogram from at least the first view dataset and the second view dataset;
      interpolate the first and second view datasets to generate interpolated pixels in an interpolated view dataset at the first kVp, using at least two pixels from each of the first and second view datasets and the reference sinogram to generate each interpolated pixel in the interpolated view dataset; and
      generate an image of the object using the interpolated view dataset.

2. The CT system of claim 1 wherein the computer is further programmed to combine at least the first view dataset, the second view dataset, and the interpolated view dataset, to form a first kVp sinogram.

3. The CT system of claim 2 wherein the computer is further programmed to acquire a third view dataset positioned between the first view dataset and the second view dataset, wherein the third view dataset is acquired with the x-ray source energized to the second kVp.

4. The CT system of claim 3 wherein the computer is programmed to generate the image of the object by being programmed to:
   generate a second kVp sinogram formed from at least the third view dataset; and
   employ a basis material decomposition algorithm that decomposes the first kVp sinogram and the second kVp sinogram.

5. The CT system of claim 3 wherein the computer is further programmed to acquire:
   the first view dataset at a first circumferential view location of the gantry,
   the third view dataset at a subsequent second circumferential view location; and
   the second view dataset at a subsequent third circumferential view location;
   wherein no view data is acquired between the first and second circumferential view locations, and no view data is acquired between the second and third circumferential view locations.

6. The CT system of claim 3 wherein the computer is programmed to acquire the first view dataset as one of a first plurality of view datasets that are acquired at subsequent neighboring view locations and at the first kVp, and the computer is programmed to acquire the second view dataset as one of a second plurality of view datasets that are acquired at subsequent neighboring view locations and at the second kVp.

7. The CT system of claim 1 wherein the computer is programmed to obtain the reference sinogram via one of a back-projection/projection method, a combination of linearly interpolated sinograms, a local window filtering method, and a linear interpolation with Wiener filtering.

8. The CT system of claim 1 wherein the computer is further programmed to calculate weighting factors for the interpolation from the reference sinogram.

9. The CT system of claim 8 wherein the computer is further programmed to minimize a minimum square error (MSE) function that is based on the reference sinogram.

10. A method of acquiring CT imaging data, the method comprising:
applying a first voltage potential between a cathode and an x-ray target to generate x-rays at the first potential;
applying a second voltage potential between the cathode and the x-ray target to generate x-rays at the second potential, wherein the second voltage potential is different from the first voltage potential;
obtaining a first view dataset and a second view dataset of imaging data from the x-rays generated at the first voltage potential and the second stage potential respectively, wherein the first view dataset and the second view dataset are obtained at respective first and second view locations that are separated by at least a third view location;
deriving a reference sinogram based on the first and second view datasets;
estimating values of a third view dataset at the third view location and at the first voltage potential using pixel data from pixel locations of each of the first and second view datasets and using weighting from the reference sinogram; and
reconstructing an image based on the third view dataset.

11. The method of claim 10 wherein estimating includes estimating values of the third view dataset based on at least two pixels from each of the first and second view datasets.

12. The method of claim 10 further comprising obtaining a fourth view dataset at the third view location from the x-rays generated at the second voltage potential.

13. The method of claim 12 comprising:
combining the first view dataset, the second view dataset, and the third view dataset to form a first-potential sinogram;
obtaining a plurality of second-potential view datasets from the x-rays generated at the second voltage potential;
combining the fourth view dataset with the plurality of second-potential view datasets to form a second-potential sinogram; and
wherein reconstructing the image comprises reconstructing a dual-energy image using the first-potential sinogram and the second-potential sinogram and a basis material decomposition algorithm.

14. The method of claim 12 wherein obtaining the first, fourth, and second view datasets comprises:
obtaining the first view dataset prior to obtaining the fourth view dataset;
obtaining the fourth view dataset prior to obtaining the second view dataset; and
obtaining the first, fourth, and second view datasets at sequential view locations.

15. The method of claim 12 wherein obtaining the first view dataset and the second view datasets comprise:
obtaining the first view dataset comprises obtaining the first view dataset as a first view dataset of a first plurality of view datasets sequentially obtained from x-rays generated via the first voltage potential; and
obtaining the second view dataset comprises obtaining the second view dataset as a first view dataset of a second plurality of view datasets sequentially obtained from x-rays generated via the second voltage potential.

16. The method of claim 15 wherein obtaining the first and second pluralities of view datasets includes obtaining an equal number of views in each of the first and second pluralities of view datasets, and wherein the first view dataset of the first plurality of view datasets is combined with the first view dataset of the second plurality of view datasets to form a first sinogram.

17. The method of claim 15 wherein deriving the reference sinogram comprises deriving the reference sinogram via one of a back-projection/projection method, a combination of linearly interpolated sinograms, a local window filtering method, and a linear interpolation with Wiener filtering.

18. A non-transitory computer readable storage medium having stored thereon a computer program comprising instructions, which, when executed by a computer, cause the computer to:
apply a first kVp potential between a cathode and a target;
apply a second kVp potential, different from the first kVp potential, between the cathode and the target;
acquire a first view dataset at a first circumferential location on a CT gantry and at the first kVp potential;
acquire a second view dataset at a second circumferential location on the CT gantry and at the second kVp potential;
derive a reference sinogram from at least the first and second acquired view datasets;
acquire a third view dataset at the second kVp potential and at a third circumferential and location on the CT gantry, wherein the third circumferential location is circumferentially located between the first circumferential location and the second circumferential location;
interpolate a fourth view dataset at the third circumferential location and at the first kVp potential, wherein the interpolation includes pixels that are each interpolated with at least two pixels of data from each of the first view dataset and the second view dataset and using weighting from the reference sinogram; and
reconstruct an image using at least the third view dataset.

19. The non-transitory computer readable storage medium of claim 18 wherein the instructions further cause the computer to acquire the first view dataset, the third view dataset, and the second view dataset in sequential respective circumferential locations about the CT gantry.

20. The non-transitory computer readable storage medium of claim 18 wherein the instructions cause the computer to obtain the reference sinogram via one of a back-projection/projection method, a combination of linearly interpolated sinograms, a local window filtering method, and a linear interpolation with Wiener filtering.

21. The non-transitory computer readable storage medium of claim 18 wherein the computer is further programmed to calculate weighting factors for interpolating the third view dataset from the reference sinogram.

* * * * *